United States Patent [19]

Blank et al.

[11] Patent Number: 4,863,642

[45] Date of Patent: Sep. 5, 1989

[54] PROCESS FOR PREPARING ACID HALIDES

[75] Inventors: Heinz U. Blank, Odenthal; Erich Wolters, Niederzier, both of Fed. Rep. of Germany

[73] Assignee: Bayer Aktiengesellschaft, Leverkusen, Fed. Rep. of Germany

[21] Appl. No.: 396,513

[22] Filed: Jul. 8, 1982

[30] Foreign Application Priority Data

Jul. 18, 1981 [DE] Fed. Rep. of Germany ....... 3128445

[51] Int. Cl.$^4$ ............................................. C07C 17/58
[52] U.S. Cl. .................................................. 562/848
[58] Field of Search ....................... 260/544 A, 544 L

[56] References Cited

U.S. PATENT DOCUMENTS 1,891,930 12/1932 Hopff et al. .
2,378,048 6/1945 Theobald ........................ 260/544 A

OTHER PUBLICATIONS

Thomas, Anhydrous Aluminum Chloride In Organic Chemistry, Reinhold Publishing Corp., pp. 765,766 (1941).
Liebigs, Annalen Der Chemie, p. 72 (1959).

Primary Examiner—Paul J. Killos
Attorney, Agent, or Firm—Sprung Horn Kramer & Woods

[57] ABSTRACT

Acid halides of the formula $(R^1, R^2, R^3)C-CO-Hal$ are obtained by reacting alkyl halides of the formula $(R^1, R^2, R^3)C-Hal$ with carbon monoxide under a pressure of 5 to 1,000 bar and at a temperature of $-20°$ C. to $+100°$ C. in the presence of 0.001 to 0.3 mol of $AlCl_3$ and/or $FeCl_3$, if appropriate in the presence of a further Bronsted or Lewis acid, per mol of the alkyl halide. The process is carried out, if desired in the presence of a solvent which is customary for Friedel-Crafts or Friedel-Crafts-related reactions and, if appropriate in the presence of a hydrogen halide. The acid chloride can be isolated from the reaction mixture or further reacted.

19 Claims, No Drawings

PROCESS FOR PREPARING ACID HALIDES

The present invention relates to a process for preparing organic acid halides by reacting alkyl halides with carbon monoxide.

Justus Liebig's Ann. 625, 66 et seq. (1959) discloses that tertiary alkyl halides react in the presence of approximately stoichiometric amounts of aluminum chloride or iron(III) chloride and under 150 bar with carbom monoxide to produce, in poor yield, t-butyl isobutenyl ketone and a small amount of pivalic acid.

According to U.S. Pat. No. 2,580,070 column 1, lines 12-21, it is very generally not possible to prepare acid chlorides in substantial yields by any method which includes the use of alkyl chlorides and carbon monoxide as starting materials and aluminum chloride as catalyst.

It is also known from U.S. Pat. No. 2,580,070 to react t-butyl chloride and t-amyl bromide with equimolar amounts of boron trifluoride at 0° C. and under a carbon monoxide pressure of 700 atmospheres to give the corresponding pivaloyl chloride or α,α-dimethylpropionyl bromide respectively, but despite the high CO pressure it was possible to react t-butyl chloride at a conversion of at most 49 mol %. Moreover, expensive working-up is necessary to recover or remove the $BF_3$. If the reaction between t-butyl chloride and carbon monoxide is carried out with 10% of bismuth trichloride or with 2% of tin tetrachloride at temperatures of 50° and 150° C., the conversions are only 5 and 0% and no pivaloyl chloride could be isolated.

A process has now been found for preparing acid chlorides of the formula

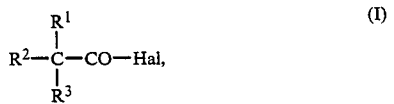

in which
$R^1$ and $R^2$ independently of one another represent branched or unbranched alkyl, halogenoalkyl, cycloalkyl, halogenocycloalkyl, optionally substituted aryl, optionally substituted aralkyl or halogen, $R^3$ represents hydrogen, branched or unbranched alkyl, halogenoalkyl, cycloalkyl, halogenocycloalkyl, optionally substituted aryl or optionally substituted aralkyl, and in which two of the radicals $R^1$, $R^2$ and $R^3$, together with the C atom on which they are substituents, can also form a ring system and
Hal represents a halogen atom,
by reacting alkyl halides of the formula

in which
$R^1$, $R^2$, $R^3$ and Hal have the meaning mentioned, with carbon monoxide under an elevated pressure and at a reduced to elevated temperature, which process is characterized in that the reaction is carried out in the presence of catalytic amounts of aluminum chloride and/or ferric chloride and, if desired, in the presence of a further Brønsted or Lewis acid and, if appropriate, in the presence of a solvent.

The acid halide can be isolated from the reaction mixture or directly reacted in the reaction mixture.

Examples which may be mentioned of a halogen atom are fluorine, chlorine and bromine atoms, preferably a chlorine or bromine atom and particularly preferably a chlorine atom.

Examples which may be mentioned of a branched or unbranched alkyl are those alkyls which have 1 to 20, preferably 1 to 10, particularly preferably 1 to 3, carbon atoms, such as methyl, ethyl, propyl, isopropyl, butyl, isobutyl, t-butyl, amyl, isoamyl, t-amyl, hexyl, isohexyl, octyl, isooctyl, decyl, isodecyl, dodecyl, isododecyl, stearyl, isostearyl, eicosyl or isoeicosyl. The unbranched alkyl radicals are preferable.

An example which may be mentioned of halogenoalkyl is alkyl which has been described and which is monosubstituted or multi-substituted by halogen, such as chloromethyl, dichloromethyl, trichloromethyl, bromomethyl, dibromomethyl, tribromomethyl, fluoromethyl, difluoromethyl, trifluoromethyl, singly or multiply chlorinated, brominated or fluorinated ethyl, propyl, butyl, hexyl, octyl, decyl, dodecyl, stearyl or eicosyl.

An example which may be mentioned of cycloalkyl is an optionally methyl- or ethyl-substituted cycloaliphatic radical having, for example, 3 to 20, preferably 4 to 12, particularly preferably 5 to 6, ring carbon atoms, such as, for example, cyclopropyl, cyclobutyl, cyclopentyl, methylcyclopentyl, ethylcyclopentyl, cyclohexyl, methylcyclohexyl, ethylcyclohexyl, cycloheptyl, cyclooctyl, cyclododecyl or cycloeicosyl.

An example which may be mentioned of halogenocycloalkyl is a singly or multiply chlorinated, brominated or fluorinated cycloalkyl as described, such as chlorocyclopentyl, chlorocyclohexyl, bromocyclopentyl or bromocyclohexyl.

Examples which may be mentioned of aryl are phenyl, naphthyl, anthryl, phenanthryl or diphenyl. The preferred aryl is phenyl.

Examples which may be mentioned of aralkyl are those aralkyls which contain in the alkyl part 1 to 4, preferably 1 to 2, carbon atoms and in the aromatic part 6 to 14 carbon atoms, such as benzyl, α-phenylethyl, β-phenylethyl, naphthylmethyl, naphthylethyl, anthrylmethyl, anthrylethyl, diphenylmethyl or diphenylethyl. The preferred aralkyl is benzyl.

Aryl or aralkyl which were just mentioned by way of example can carry in their aromatic parts substituents such as fluorine, chlorine, bromine, iodine, $C_1-C_4$-alkyl or nitro. Such radicals can be present singly or multiply, if desired also in combinations. Such substituents are preferably called fluorine, chlorine and bromine.

Furthermore, 2 of the radicals $R^1$, $R^2$ and $R^3$, together with the C atom on which they are substituents, can form a ring system. Such a ring system has, for example, 3 to 12, preferably 5 to 6, C atoms. Examples of such ring systems are cyclopropane, cyclobutane, cyclopentane, cyclohexane, cycloheptane, cyclooctane and cyclododecane.

Preferably used in the process according to the invention are alkyl halides of the formula

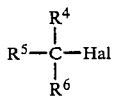

(III)

in which
R⁴ represents branched or unbranched alkyl, halogenoalkyl, cycloalkyl, aryl, halogen-substituted aryl or halogen-substituted aralkyl,
R⁵ denotes branched or unbranched alkyl, halogenoalkyl, cycloalkyl, aryl or halogen and
R⁶ represents hydrogen, branched or unbranched alkyl or cycloalkyl, and in which 2 of the substituents R⁴, R⁵ and R⁶, together with the C atom on which they are substituents, can also form a ring system and
Hal has the abovementioned meaning.

Particularly preferably used are alkyl halides of the formula

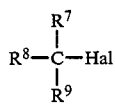

(IV)

in which
R⁷, R⁸ and R⁹ independently of one another denote branched or unbranched, optionally halogen-substituted alkyl or cycloalkyl and 2 of the substituents R⁷, R⁸ and R⁹, together with the C atom on which they are substituents, can also form a ring system and
Hal has the abovementioned meaning.

Very particularly preferably used, according to the invention, are alkyl halides of the formula

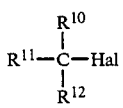

(V)

in which
R¹⁰, R¹¹ and R¹² independently of one another denote unbranched alkyl radicals and
Hal has the abovementioned meaning.

In the formulae (I), (II), (III), (IV) and (V), the preferred halides are bromides or chlorides and the chlorides are very particularly preferable.

Examples of alkyl halides which can be used according to the invention are t-butyl chloride, t-amyl bromide, 2-chloro-2-methylhexane, 2-bromo-2-ethylpentane, 2-chloro-2-propylhexane, 1-chloro-1-methylcyclopropane, 1-chloro-1-methylcyclopentane, 1-chloro-1-methylcyclohexane, 1--bromo-1-methylcyclohexane, 1-bromo-1-methylcyclododecane, 1,2-dichloro-2-methylpropane, 1,2-dichloro-2-chloromethylbutane, 1,2,3-trichloro-3-methylbutane, 1,2-dichloro-2-benzylpropane, 1,2-dibromo-2-(2-phenylethyl)-propane, 1,2-dibromo-2-methylpropane, 2-chloro-2-(2-chlorocyclohexyl)-propane, 1,2-dichloro-2-(2-chlorocyclohexyl)-butane, 1,2,3-trichloro-2-chloromethylpropane, and 1,2,3-trichloro-2-methylpropane.

The process according to the invention is carried out under a carbon monoxide pressure which can vary within wide limits, for example from 5 to 1,000 bar. The process can also be carried out above the range mentioned and the upper limit is provided only by the amount of technical effort considered suitable. Below 5 bar conversions become markedly lower. The CO pressure used is preferably 25 to 250 bar, particularly preferably 50 to 150 bar.

Examples which may be mentioned of the temperature range within which the process according to the invention is carried out are $-20°$ to $+100°$ C., preferably $-20°$ to $+50°$ C., particularly preferably $-10°$ to $+10°$ C. and very particularly preferably $0°$ to $+5°$ C. In many cases, yield and selectivity decrease somewhat with increasing temperature, so that lower temperatures are generally more favourable. However, usually it is not necessary to use temperatures below $-10°$ C. If the reaction is carried out within the particularly preferred temperature range of $-10°$ to $+10°$ C., in particular $0°$ to $+5°$ C., it is advantageous to carry out a secondary reaction, subsequent to the reaction step, at elevated temperatures of $10°$–$100°$ C., in particular $20°$–$50°$ C., and to work up only subsequently to this secondary reaction step.

The optimum temperature can readily be determined by simple preliminary experiments, as a function of the alkyl halide used, of the catalyst system and of the solvent.

The process according to the invention is carried out by means of $AlCl_3$ and/or $FeCl_3$ as catalyst and, if appropriate, in the presence of a further Brönsted or Lewis acid. Examples which may be mentioned of the latter are halides of the elements, particularly of metals, of the third, fourth and fifth main group and of the first, second, fourth, fifth, sixth, seventh and eighth secondary group of the periodic system of the elements (Mendeleev), for example iron(III) bromide, zinc chloride, zinc bromide, boron chloride, gallium chloride, titanium tetrachloride, antimony(III) chloride, antimony(V) chloride, antimony(III) bromide and antimony(V) bromide. The halides mentioned can be used on their own or as a mixture of those mentioned, in each case in anhydrous form. Halides of metals of the first and the second main group of the periodic system, such as lithium chloride, sodium chloride or magnesium chloride, can be added to these halides. Halides of the type mentioned or mixtures of the type mentioned can also be used supported on a material such as aluminum oxide, silica gel or activated carbon. Aluminum chloride or iron(III) chloride without additives, particularly aluminum chloride, is preferably used.

According to the invention, $AlCl_3$ and $FeCl_3$ are used in catalytic amounts. Examples which may be mentioned of the latter are an amount up to 0.3 mol, preferably 0.005 to 0.2 mol, particularly preferably 0.01 to 0.1 mol, per mol of alkyl halide. It is also possible to carry out the reaction of the process according to the invention in the presence of a hydrogen halide, for example hydrogen chloride, in an amount of 0.005 to 2 mols, preferably 0.01 to 0.1 mol, per mol of alkyl halide. Larger amounts of a hydrogen halide than those indicated are not critical for the process according to the invention.

In the case where the reaction is carried out in the presence of a hydrogen halide it is also possible to use, instead of the alkyl halides, parent olefins which can form the alkyl halides by adding hydrogen halide. This requires of course an at least equimolar amount of a hydrogen halide, relative to the olefin. Such olefins may be, e.g. represented by the formula

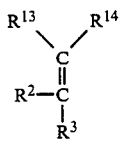

(IV)

wherein

R² and R³ have the above mentioned meaning and
R¹³ and R¹⁴ denote independently from another hydrogen, $C_1$–$C_4$-alkyl, $C_1$–$C_4$-halogenoalkyl or both R¹³ and R¹⁴ together with the C-atom which they substitute denote $C_5$–$C_6$-cycloalkyl.

It is preferred that at least one of R¹³ and R¹⁴ denotes hydrogen.

The process according to the invention can be carried out with or without solvent. The variant without solvent is possible whenever the alkyl halide used is liquid at the reaction temperature chosen. In the event that a solvent is used, generally a solvent may be mentioned which is customary for Friedel-Crafts type reactions. Examples of suitable organic solvents are halogenated hydrocarbons, such as dichloroethane, trichloroethane, tetrachloroethane, methylene chloride, chlorobenzene, dichlorobenzene or trichlorobenzene, furthermore carbon disulphide, benzenesulphonic acid, methanesulphonic acid, trifluoromethanesulphonic acid, perfluorobutanesulphonic acid, perfluoroctanesulphonic acid, trifluoroacetic acid, alkanes, such as hexane, octane or isododecane, and nitrobenzene. Examples of suitable inorganic solvents are $SO_2$, HCl, HF, $H_2SO_4$, $PCl_3$ and $POCl_3$. These solvents can be used on their own or in mixtures. Preferred solvents are chlorinated hydrocarbons, such as methylene chloride, dichloroethane, dichlorobenzene or trichlorobenzene. To carry out the process according to the invention in the presence of a solvent is preferable. Examples which may be mentioned of the amount of solvent to be used are 20 to 500% by volume, preferably 50 to 250% by volume, and particularly preferably 80 to 150% by volume, relative to the volume of the alkyl halide used.

The process according to the invention can be carried out, for example, as follows:

The solvent together with the catalytic amount of the catalyst is initially introduced into a V4A stainless steel autoclave. The desired CO pressure is then injected and the alkyl halide, undiluted or diluted with the solvent, is pumped in with thorough stirring. The CO pressure is maintained by replenishing the CO, for example via a reducing valve. Since in general the reaction proceeds very rapidly, more alkyl halide can be rapidly pumped in or the reaction can advantageously be carried out even continuously. After a short period of further stirring, no more CO is taken up, and the reaction can be discontinued. The reaction mixture, which, in addition to the solvent, contains virtually only acid halide and possibly some residual alkyl halide, can either be used in this form for subsequent reactions of the acid chloride, for example for preparing the acid or its derivatives such as esters, amides or peroxides, or be worked up to pure acid chloride. The latter step is possible in a simple manner, for example by means of distillation, in particular when a solvent is used which has a favourable boiling point in respect of distillative separation into constituents.

The top product of such a distillation comprises unreacted alkyl halide, the solvent used and the acid halide desired, if desired, when the distillation is carried out in the corresponding manner, as fractions already present in the pure state.

It is possible, in a way which is favourable and surprising according to the findings of the literature, to prepare the desired acid halides by means of the process according to the invention with up to 80% selectivity, in many cases up to 90% selectivity, and in high yield.

EXAMPLES 1–18

185 ml of the solvent indicated in the table and the amount and type indicated in the table of catalyst are initially introduced into a 0.7 l V4A stainless steel autoclave. 185 g (217 ml; 2.0 mols) of t-butyl chloride are pumped in in the course of 20 minutes with stirring at the temperature indicated in the table and under the CO pressure indicated there. The particular CO pressure is maintained at a constant value by replenishing CO via a reducing valve. After the period of further stirring indicated in the table, no more CO is taken up. The autoclave pressure is let down, and the reaction mixture is distilled via a 30 cm Vigreux column. The yields shown in the table are obtained.

| Example Number | Catalyst Type | g (Mol %) | T °C. | pCO bar | t min | Solvent | t-Butyl chloride g (% of theory) | Pivaloyl chloride g (% of theory) | Conversion % | Selectivity % |
|---|---|---|---|---|---|---|---|---|---|---|
| 1 | AlCl₃ | 2.7 (1.0) | 0–3 | 140 | 15 | 1,3,4,-Trichlorobenzene | 69.7 (37.7) | 134.9 (56.0) | 62.3 | 89.9 |
| 2 | " | 9.3 (3.5) | " | " | " | " | 33.3 (18.0) | 166.3 (69.0) | 82.0 | 84.2 |
| 3 | " | 26.7 (10.0) | " | " | " | " | 32. (17.3) | 106.4 (44.2) | 82.7 | 53.4 |
| 4 | " | 80.0 (30.0) | " | " | " | " | 1.2 (0.7) | 12.0 (5.0) | 99.3 | 5.0 |
| 5 | " | 9.3 (3.5) | " | 150 | " | " | 22.2 (12.0) | 171.1 (71.0) | 88.0 | 80.0 |
| 6 | " | " | " | 250 | " | " | 18.5 (10.0) | 176.3 (73.1) | 90.0 | 81.2 |
| 7 | " | " | " | 90 | 30 | " | 34.8 (18.8) | 146.0 (60.5) | 81.2 | 74.6 |
| 8 | " | " | " | 50 | 45 | " | 75.8 (41.0) | 92.4 (38.3) | 59.0 | 65.0 |
| 9 | " | " | " | 10 | 15 | " | 120.3 (65.0) | 17.7 (7.3) | 35.0 | 21.0 |
| 10 | " | " | " | 5 | 15 | " | 152.6 (82.4) | 2.4 (1.0) | 17.6 | 5.7 |
| 11 | " | " | 10 | 100 | 30 | " | 49.4 (26.7) | 129.3 (53.7) | 73.3 | 73.2 |
| 12 | " | " | 20 | " | " | " | 62.3 (33.7) | 24.0 (10.0) | 66.3 | 15.0 |
| 13 | " | " | 50 | " | " | " | 115.8 (62.6) | 8.2 (3.4) | 37.4 | 9.1 |
| 14 | " | " | −10 | " | " | 1,2-Dichlorobenzene | 55.3 (29.9) | 144.1 (59.8) | 70.1 | 85.3 |
| 15 | " | " | 0–3 | 140 | 15 | Methylene chloride | 37.4 (20.2) | 164.6 (68.3) | 79.8 | 85.6 |
| 16 | FeCl₃ | 11.4 (3.5) | " | " | " | Trichlorobenzene | 77.7 (42.0) | 86.8 (36.0) | 58.0 | 62.1 |
| 17 | AlCl₃ | 1.4 (0.5) | " | 150 | " | " | 110.0 (59.5) | 89.6 (37.2) | 40.5 | 91.8 |
| 18 | " | 53.3 (20.0) | −10–0 | " | " | Dichlorobenzene | 16.3 (8.8) | 63.1 (26.2) | 91.2 | 28.8 |

EXAMPLE 19

833 ml (1,205 g) of 1,2,4-trichlorobenzene and 42.0 g (0.31 ml) of AlCl$_3$ are initially introduced into a 2.7 l V4A stainless steel autoclave. 832.5 g (9.0 mols) of t-butyl chloride are pumped in with stirring in the course of 10 minutes at a temperature of 5° C. and under a CO pressure of 150 bar. The CO pressure is maintained at 150 bar by replenishing CO via a reducing valve. After 10 minutes' further stirring, the mixture is heated for 30 minutes at 50° C. This increases the pressure in the autoclave to about 165 bar.

After cooling down, the reaction mixture is distilled. This produces 110.7 g of t-butyl chloride (13.3%) and 797.1 g of pivaloyl chloride (73.5%).

A selectivity of 84.8% is obtained at a conversion of 86.7%.

EXAMPLE 20

185 ml (268 g) of trichlorobenzene and 13.3 g (0.1 mol) of AlCl$_3$ are initially introduced into a 0.7 l V4A stainless steel autoclave. 254.0 g (2.0 mols) of 1,2-dichloro-2-methylpropane are pumped in with stirring in the course of 20 minutes at 0°–3° C. and under 120 bar of CO. The CO pressure is maintained at a constant value by replenishing CO via a reducing valve. After 20 minutes no more CO is taken up. The autoclave pressure is let down, and the dark yellow reaction mixture is distilled via a 30 cm Vigreux column. 50.3 g of 1,2-dichloro-2-methylpropane and 208.6 g of chloropivaloyl chloride are obtained. This corresponds to a conversion of 80.2% and a selectivity of 83.9%.

EXAMPLE 21

185 ml (268 g) of trichlorobenzene and 13.3 g (0.1 mol) of AlCl$_3$ are initially introduced into a 0.7 l V4A stainless steel autoclave. HCl is pumped in at 0°–3° C. up to a pressure of 20 bar. 181.0 g (2.0 mols) of methallyl chloride is then pumped in with stirring. The HCl pressure is maintained by replenishing with HCl. Further stirring is carried out for 20 minutes. The pressure is then increased to 140 bar by injecting 120 bar of CO and maintained at this level by replenishing with CO. After 1 hour, no more CO is taken up. The autoclave contents are distilled. 54.7 g of 1,2-dichloro-2-methylpropane and 198.4 g of chloropivaloyl chloride are obtained. This corresponds to a conversion of 78.5% and a selectivity of 81.5%.

What is claimed is:

1. A process for preparing an acid halide of the formula $$R^2-\underset{\underset{R^3}{|}}{\overset{\overset{R^1}{|}}{C}}-CO-Hal$$

in which

R$^1$ and R$^3$ independently of one another represent branched or unbranched alkyl, halogenoalkyl, cycloalkyl or halogenocycloalkyl and two of the radicals R$^1$, R$^2$ and R$^3$, together with the C atom on which they are substituents, can form a ring system and Hal represents a halogen atom which comprises contacting an alkyl halide of the formula

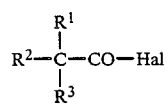

wherein

R$^1$, R$^2$, R$^3$ and Hal have the meanings given above at −20° C. to below +20° C. with carbon monoxide under an elevated pressure in the presence of a catalytic amount of aluminum chloride, ferric chloride or a mixture thereof, wherein there is additionally present a further Bronsted or Lewis acid.

2. A process for preparing an acid halide which comprises contacting an olefin of the formula

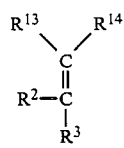

in which

R$^2$ and R$^3$ have the meaning given in claim 1 and R$^{13}$ and R$^{14}$ denote independently from one another hydrogen, C$_1$–C$_4$-alkyl, C$_1$–C$_4$-halogenoalkyl or both R$^{13}$ and R$^{14}$ together with a C-atom on which they are substituents denote C$_5$–C$_6$-cycloalkyl in the presence of at least equimolar amounts of a hydrogen halide, relative to the olefin, with carbon monoxide in the presence of a catalytic amount of aluminum chloride, ferric chloride or mixture thereof, wherein the combined amount of aluminum chloride and ferric chloride is up to 0.3 mol per mol of alkyl halide.

3. A process according to claim 2, wherein the combined amount of aluminum chloride and ferric chloride is 0.005 to 0.2 mol per mol of alkyl halide.

4. A process for preparing an acid halide of the formula

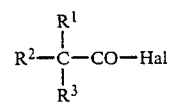

in which

R$^1$ and R$^3$ independently of one another represent branched or unbranched alkyl, halogenoalkyl, cycloalkyl or halogenocycloalkyl and two of the radicals R$^1$, R$^2$ and R$^3$, together with the C atom on which they are substituents, can form a ring system and Hal represents a halogen atom which comprises contacting an alkyl halide of the formula

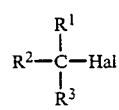

wherein

R$^1$, R$^2$, R$^3$ and Hal have the meanings given above at −20° C. to below +20° C. with carbon monoxide under an elevated pressure in the presence of a catalytic amount of aluminum chloride, ferric chloride or a mixture thereof, wherein the combined amount of aluminum chloride and ferric chloride is less than 10 mol percent, based upon the number of mols of alkyl halides.

5. A process according to claim 3, wherein the process is carried out in the presence of aluminum chloride, ferric chloride or mixture thereof in a combined amount of up to 3.5 mol percent relative to mols of alkyl halide.

6. A process according to claim 3, wherein the combined amount of aluminum chloride and ferric chloride is up to 0.3 mol per mol of alkyl halide.

7. A process according to claim 3, wherein the combined amount of aluminum chloride and ferric chloride is 0.005 to 0.2 mol per mol of alkyl halide.

8. A process according to claim 4, wherein the process is carried out in the presence of aluminum chloride.

9. A process according to claim 4, wherein the process is carried out in the presence of ferric chloride.

10. A process according to claim 1, wherein the process is carried out in the presence of a solvent.

11. A process according to claim 1, wherein the process is carried out in the presence of 20 to 500% by volume of a solvent, relative to the volume of the alkyl halide.

12. A process according to claim 28, wherein the process is carried out in the presence of 80 to 150% by volume of solvent.

13. A process according to claim 28, wherein the solvent is a chlorinated hydrocarbon.

14. A process according to claim 1, wherein the process is carried out at a CO pressure of 25 to 250 bar.

15. A process according to claim 1, wherein the process is carried out a pressure of 50–250 bar CO.

16. A process according to claim 1, wherein the process is carried out a pressure of 50–150 bar.

17. A process according to claim 1, wherein said alkyl halide is tertiary butyl chloride.

18. A process according to claim 1, wherein said alkyl halide is 1,2-dichloro-2-methyl propane.

19. A process according to claim 1, wherein said alkyl halide is methallyl chloride.

* * * * *